United States Patent [19]
Liu

[11] Patent Number: 5,885,253
[45] Date of Patent: Mar. 23, 1999

[54] AUTOMATIC SAFETY INFUSION CATHETER NEEDLE

[76] Inventor: Wen-Neng Liu, 19508 Nicholas Ave. Cerritos La., Los Angeles, Calif. 90701

[21] Appl. No.: 115,602

[22] Filed: Jul. 15, 1998

Related U.S. Application Data

[63] Continuation-in-part of Ser. No. 89,260, Jun. 3, 1998.
[51] Int. Cl.[6] .................................................. A61M 5/178
[52] U.S. Cl. ............................................ 604/164; 604/167
[58] Field of Search ..................................... 604/164, 165, 604/167, 168, 174, 177, 263, 264, 170

[56] References Cited

U.S. PATENT DOCUMENTS

| | | | |
|---|---|---|---|
| 5,279,570 | 1/1994 | Dombrowski et al. | 604/164 |
| 5,300,032 | 4/1994 | Hibbs | 604/164 |
| 5,681,288 | 10/1997 | Schlitt | 604/164 |
| 5,797,882 | 8/1998 | Purdy et al. | 604/164 |

*Primary Examiner*—John D. Yasko
*Attorney, Agent, or Firm*—Rosenberg, Klein & Bilker

[57] ABSTRACT

An automatic safety infusion catheter needle including: a trifurcate connector having a first and a second connecting sections coaxially aligned with each other. An infusion soft needle inserted on the first connecting section of the trifurcate connector. A steel needle having a needle body slidably fitted in a sleeve and axially passed in the soft needle. The sleeve is connected with the second connecting section of the trifurcate connector. The holder body of the steel needle has a projecting post formed with an air guiding hole for exhausting the air outside and making the liquid medicine smoothly flow into the soft needle. An infusion catheter is serially connected with a third connecting section of the trifurcate connector for infusion of liquid medicine through the soft needle into the body of a patient.

7 Claims, 8 Drawing Sheets

AUTOMATIC SAFETY INFUSION CATHETER NEEDLE

CROSS-REFERENCE TO RELATED APPLICATION

This application ia a Continuation-in-Part Application of U.S. Pat. Application Ser. No. 09/089,260, entitled "An automatic Safety Infusion Catheter Needle", filed on 3 Jun. 1998.

BACKGROUND OF THE INVENTION

1. Field of the Invention

The present invention relates to an automatic safety infusion catheter needle.

2. Description of the Prior Art

The existing infusion catheter needle employs one single injection needle for intravenous injection. As shown in FIG. 1, such catheter needle includes an infusion soft needle 100 and a steel needle 200. The needle body 200a of the steel needle 200 is passed through the needle body 100a of the soft needle 100 for hardening the soft needle body 100a, whereby the soft needle body 100a can be smoothly thrusted into the vein of a patient. After the soft needle body 100a is thrusted into the vein, the medical personnel must press the soft needle body 100a with one hand F to avoid back flow of the blood of the patient and draw the steel needle 200 backward from the soft needle 100 with the other hand. Then an infusion catheter 300 is serially connected with the soft needle 100 to complete the injection procedure. In use, the above catheter needle has some shortcomings as follows:

1. When pressing the soft needle body 100a with one hand, the medical personnel must draw the steel needle 200 from the soft needle 100 with the other hand. Moreover, the medical personnel must then connect the infusion catheter 300 with the soft needle 100. It is quite inconvenient to perform all these procedures at the same time.

2. After the steel needle 200 is drawn from the soft needle 100, the steel needle 200 is exposed outside and tends to impale the medical personnel. Therefore, the medical personnel may be infected with AIDS, hepatitis, etc. This is extremely dangerous to the medical personnel.

SUMMARY OF THE INVENTION

It is therefore a primary object of the present invention to provide an automatic safety infusion catheter needle which is able to avoid impalement of medical personnel and ensure the safety in medical waste processing. In addition, the automatic safety infusion catheter needle enables the medical personnel to perform the injection procedure more easily and leisurely.

According to the above object, the automatic safety infusion catheter needle of the present invention includes: a trifurcate connector having a first and a second connecting sections coaxially aligned with each other, a free end of the second connecting section being inserted with a rubber cap; an infusion soft needle fitted with the first connecting section of the trifurcate connector; and a steel needle including a holder body slidably fitted in a sleeve. A top section of the sleeve is fitted with the second connecting section of the trifurcate connector. The steel needle has a projecting post upward axially extending from top end of the holder body. The projecting post is formed with an air guiding hole for exhausting the air outside and making the liquid medicine smoothly flow into the soft needle. The needle body of the steel needle axially upward extends from the projecting post and slidably fitted in the soft needle body of the soft needle. An infusion catheter is connected with a third connecting section of the trifurcate connector for infusion of liquid medicine through the soft needle into the body of a patient. Accordingly, in injection, the soft needle together with the needle body of the steel needle is thrusted into the vein of the patient. Then the steel needle is withdrawn from the rear side of the sleeve to retract and locate and hide the needle body of the steel needle in the sleeve so as to avoid impalement and infection of the medical personnel. In addition, the medical personnel can perform the injection procedure leisurely.

The present invention can be best understood through the following description and accompanying drawings, wherein:

DETAILED DESCRIPTION OF THE PREFERRED EMBODIMENTS

Figure 1:
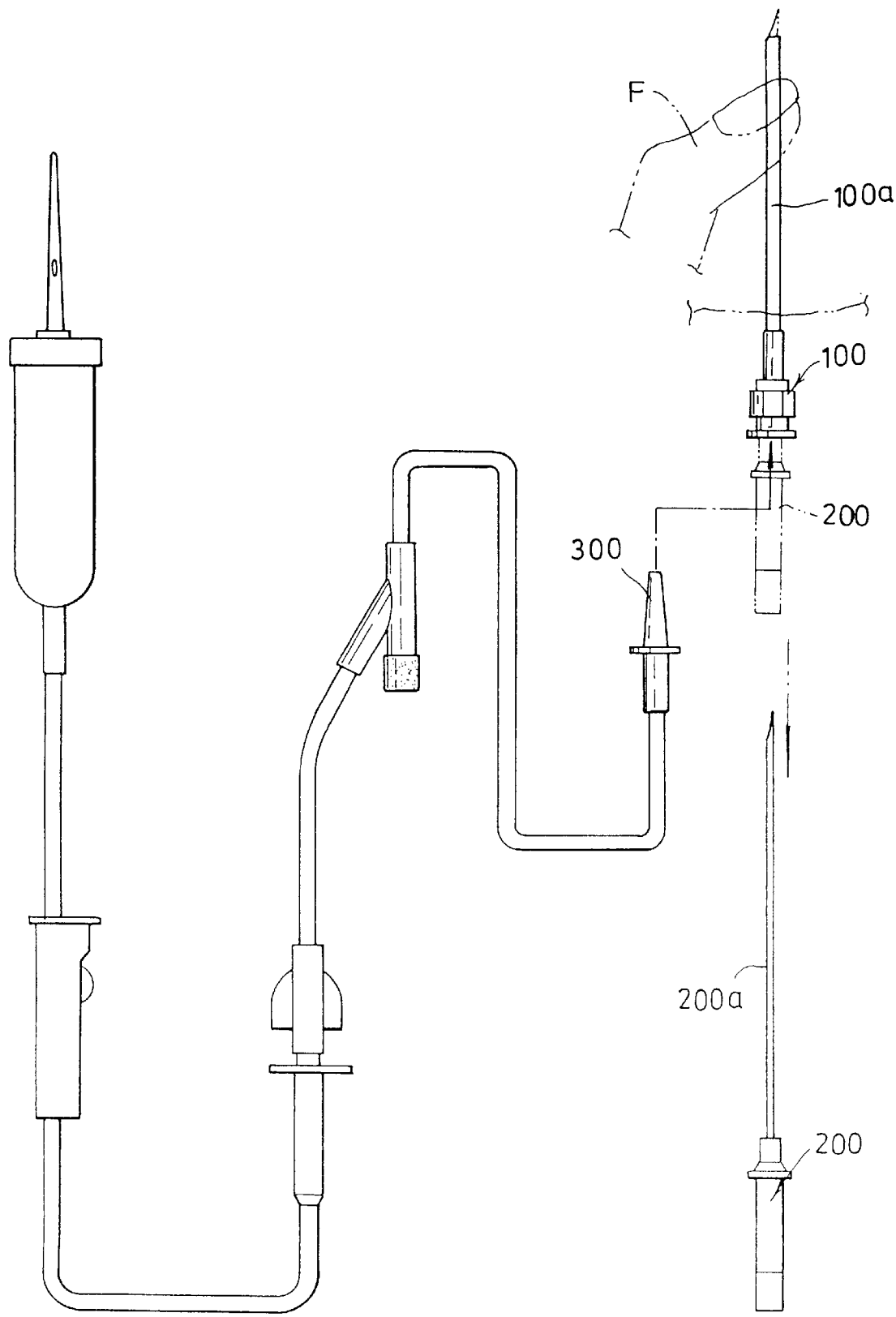
FIG. 1 shows a conventional intravenous catheter needle.
Figure 2:
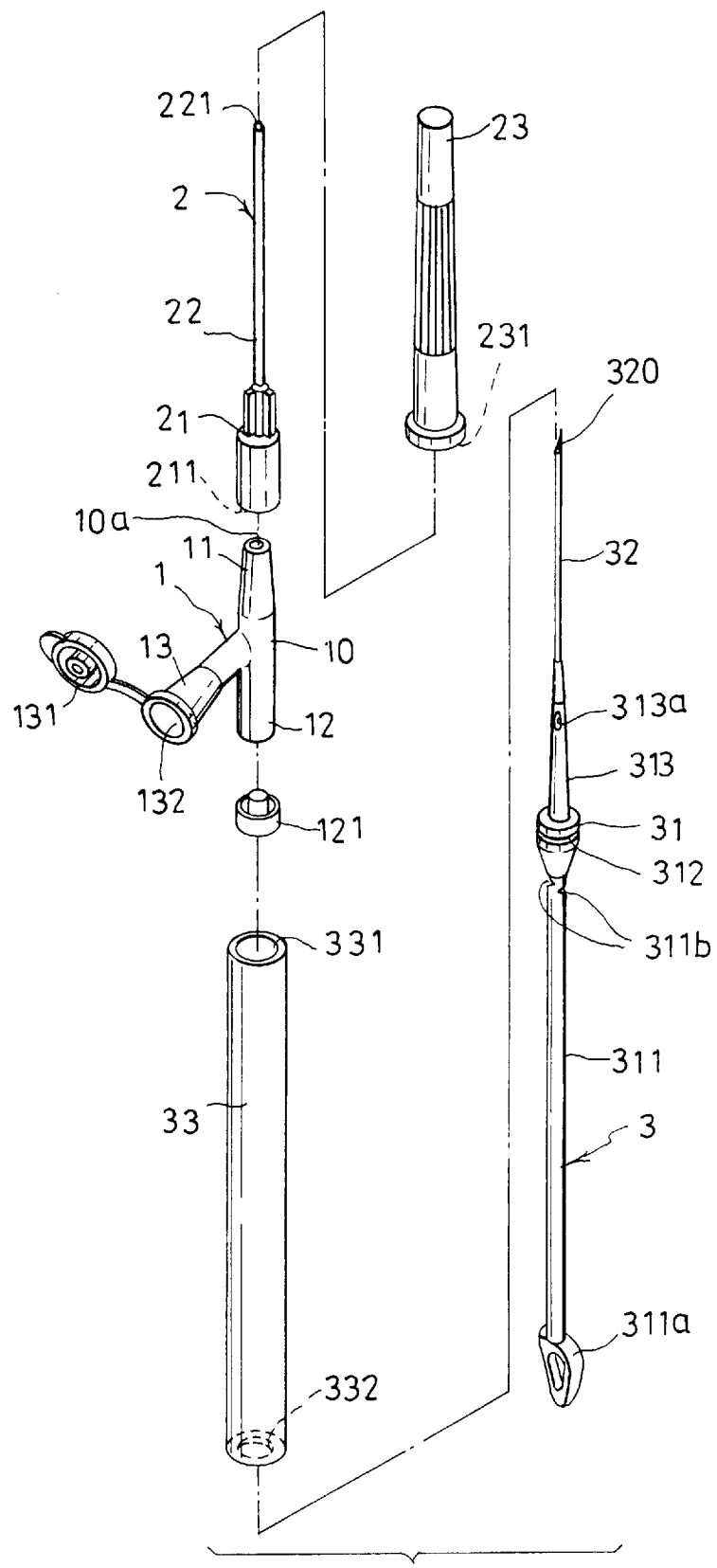
FIG. 2 is a perspective exploded view of the present invention.
Figure 3:
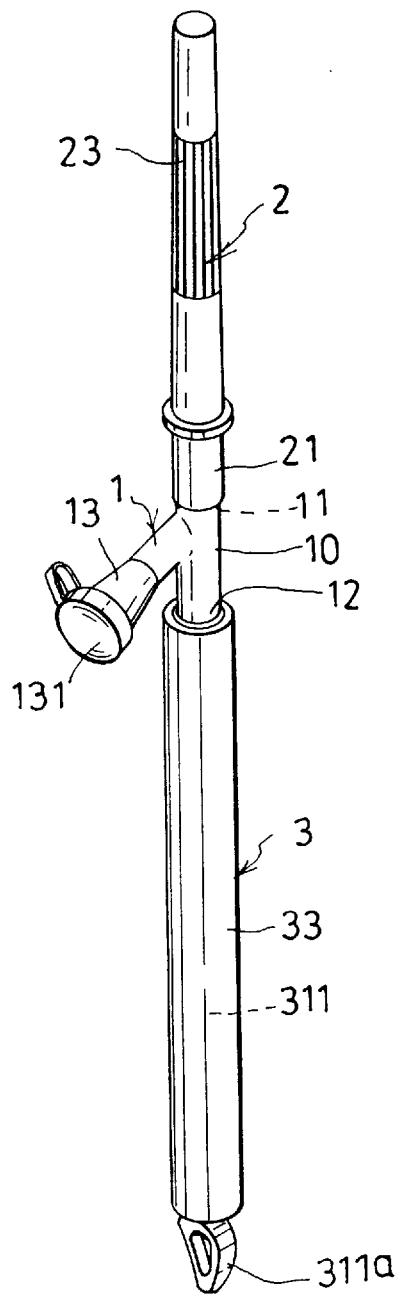
FIG. 3 is a perspective assembled view of the present invention.

Please refer to FIGS. 2 to 7. The present invention includes: a trifurcate connector 1 having a first and a second connecting sections 11, 12 coaxially aligned with each other, the end of the second connecting section 12 being fitted with a rubber cap 121; an infusion soft needle 2 inserted on the first connecting section 11 of the trifurcate connector 1; a steel needle 3 having a needle body 32 slidably fitted in a sleeve 33 and axially passed in the soft needle 2; and an infusion catheter 4 serially connected with a third connecting section 13 of the trifurcate connector 1 for infusion of liquid medicine through the soft needle 2 into the body of a patient. Accordingly, in injection, the soft needle 2 together with the needle body 32 of the steel needle 3 is thrusted into the vein of the patient. Then the steel needle 3 is withdrawn from the rear side of the sleeve 33 to retract and locate and hide the needle body 32 of the steel needle 3 in the sleeve 33. Therefore, the needle body 32 of the steel needle 3 is prevented from being exposed outside so as to avoid impalement and infection of the medical personnel. In addition, the medical personnel can perform the injection procedure leisurely.

The trifurcate connector 1 is made of plastic material, including a main body 10. An upper section of the main body 10 is defined as the first connecting section 11. A lower section of the main body 10 is defined as the second connecting section 12. The end of the second connecting section 12 is fitted with the rubber cap 121. The first and second connecting sections 11, 12 are coaxially aligned with each other about the central axis 10a of the main body 10. The third connecting section 13 outward projects from a middle section of the main body. An outer cap 131 is connected with outer edge of the third connecting section 13 for normally sealing an opening 132 of the third connecting section 13.

Referring to FIGS. 2 to 5, the infusion soft needle 2 includes: a needle holder 21 formed with a fitting socket 211 at bottom end for fitting with the first connecting section 11 of the trifurcate connector; a soft needle body 22 upward extending from the top end of the needle holder 21 and formed with an axial injection passage 221; and a needle sheath 23 formed with a protective cavity 231 for fitting around the needle holder 21 to enclose the soft needle body 22.

The steel needle 3 includes: a holder body 31 having a pulling rod 311 axially extending from the bottom end thereof, the holder body 31 being disposed with at least one engaging section 312, a projecting post 313 upward axially extending from the holder body 31 for fitting into the second connecting section 12 of the trifurcate connector 1, a top end of the projecting post 313 being formed with a radial air guiding hole 313a which is normally positioned above the rubber cap 121; a needle body 32 inserted in the projecting post 313 of the holder body 31 and axially upward extending for slidably fitting into the soft needle body 22 of the soft needle 2, a central through hole 320 of the needle body 32 being communicated with the air guiding hole 313a of the projecting post 313, whereby the air in the trifurcate connector can be exhausted through the air guiding hole 313a and the central through hole 320 of the needle body 32; and a sleeve 33 formed with a fitting hole 331 for fitting around the holder body 31 to enclose the needle body 32. The top section of the fitting hole 331 is snugly fitted around the rubber cap 121 of the second connecting section 12 of the trifurcate connector 1. The inner wall of the fitting hole 331 is formed with at least one latch section 332 for latching with the engaging section 312 of the holder body 31.

Figure 7:
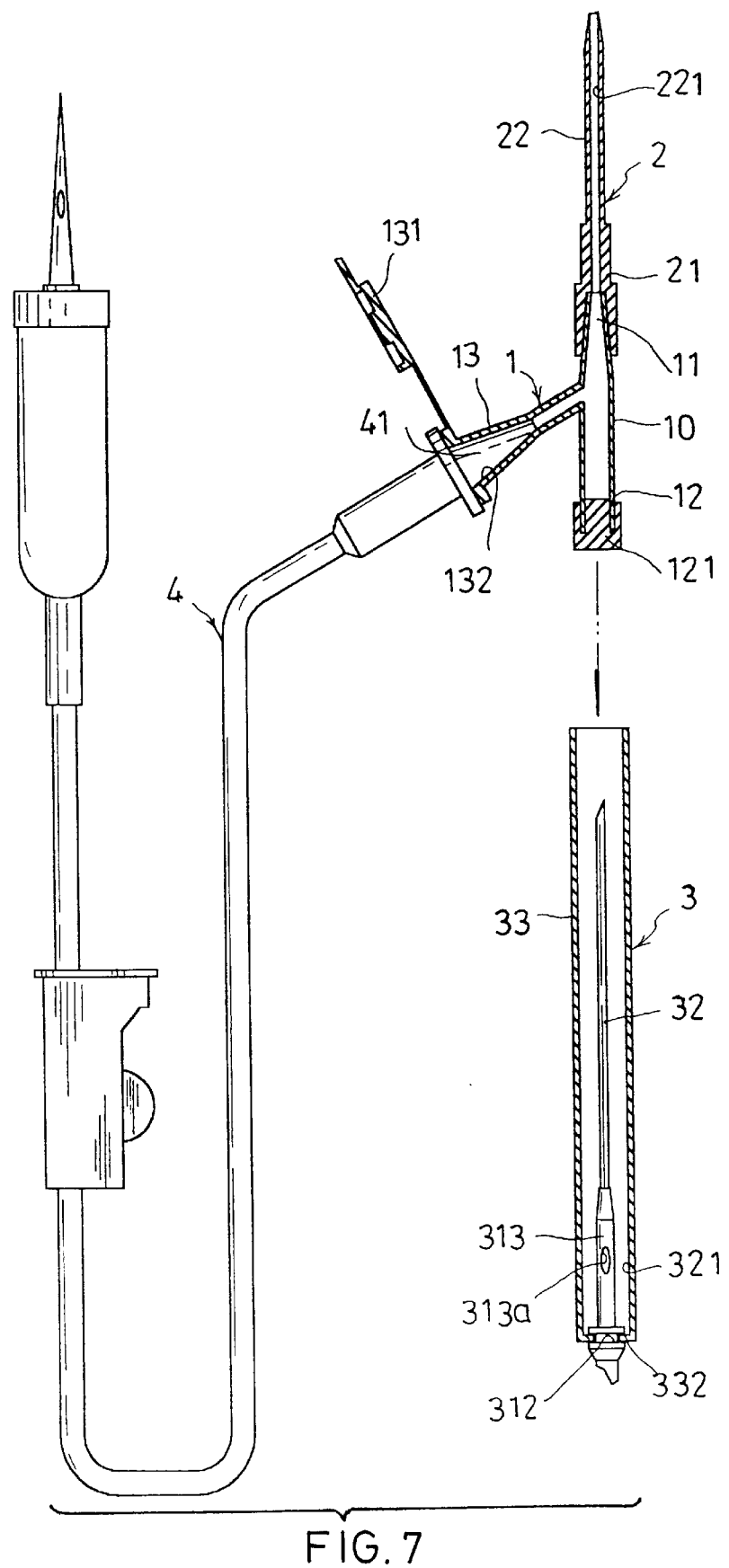
FIG. 7 is a view according to FIG. 6, showing that the steel needle and the sleeve are detached from the soft needle.
Figure 8:
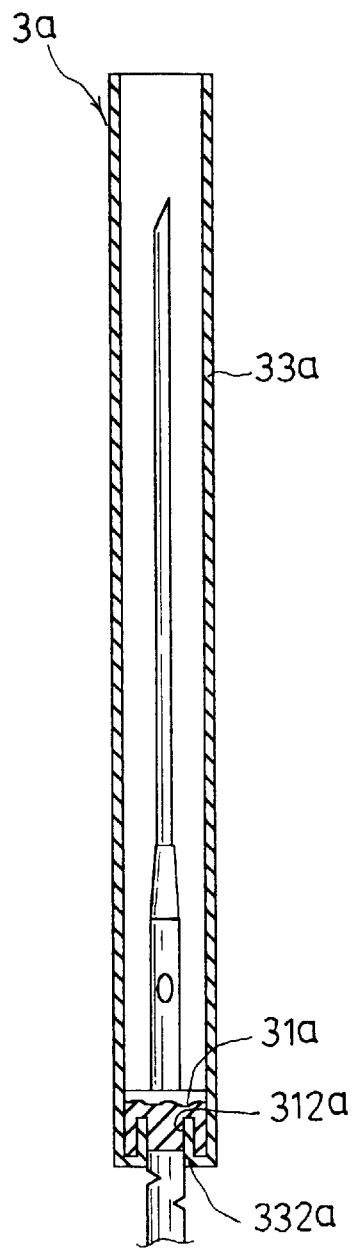
FIG. 8 is a sectional view of a second embodiment of the present invention.
Figure 9:
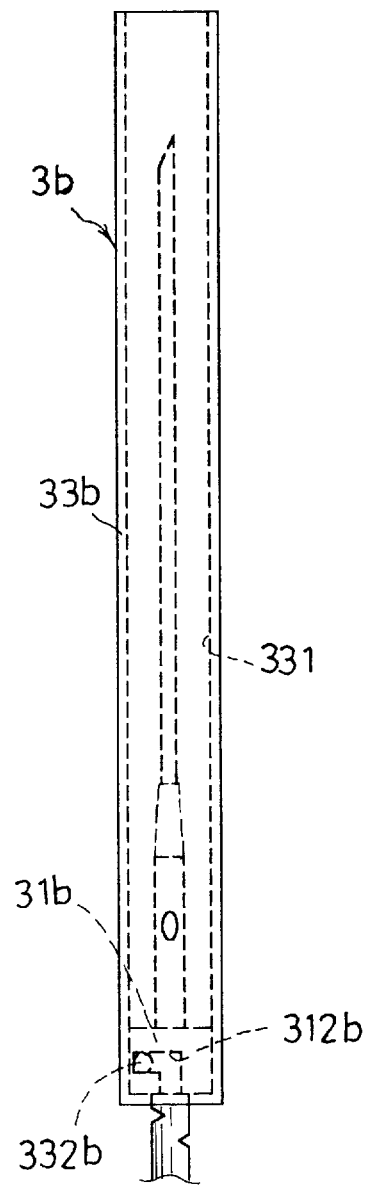
FIG. 9 is a sectional view of a third embodiment of the present invention.

The free end of the pulling rod 311 of the holder body 31 of the steel needle 3 is connected with a handle section 311a extending out of the sleeve 33 at normal time. Via the handle section 311a, the medical personnel can pull back the needle body 32. As shown in FIGS. 2 to 7, the engaging section 312 of the holder body 31 can be in the form of an annular groove formed on the holder body 31. The latching section 332 of the sleeve 33 can be in the form of an inward extending flange formed on bottom edge of the fitting hole 331. When the holder body 31 together with the needle body 32 is slided downward, the annular groove (the engaging section 312) can be snugly engaged with the flange (the latching section 332) of the sleeve 33. Therefore, the needle body 32 can be firmly located and hidden in the sleeve 33 without protruding outside to impale persons. As shown in FIG. 8, in a second embodiment of the present invention, the engaging section 312a of the holder body 31a of the steel needle 3a is in the form of an annular insertion recess formed on the bottom thereof, while the latching section 332a of the sleeve 33a is in the form of an annular upward projecting wall formed on the bottom end thereof. The projecting wall can be snugly inserted into the insertion recess to engage the holder body 31a with the sleeve 33a. FIG. 9 shows a third embodiment of the present invention, in which the engaging section 312b of the holder body 31b is in the form of an L-shaped cavity formed on the periphery thereof, while the latching section 332b of the sleeve 33b is in the form of a projecting pin. The engaging section 312b of the holder body 31b can be slided downward and rotated to engage with the latching section 332b of the sleeve 33b. The measure for engagement between the holder body and the sleeve is not limited in the present invention.

Figure 6:
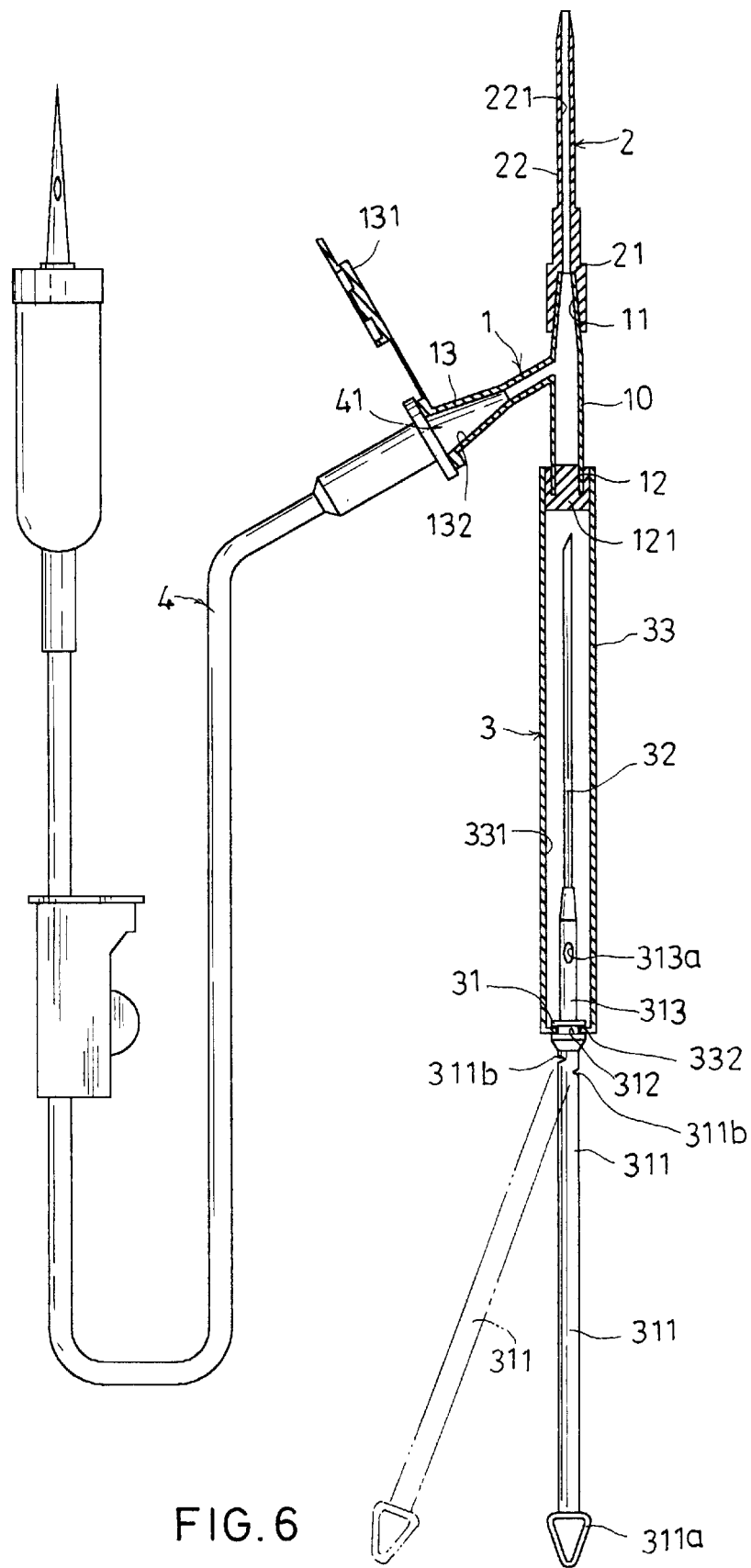
FIG. 6 is a view according to FIG. 4, showing that the steel needle is pulled backward and located and hidden in the sleeve.

The pulling rod 311 of the holder body 31 is formed with at least one breaking notch 311b, whereby after the pulling rod 311 is pulled back, the pulling rod 311 can be bent and broken at the breaking notch 311b shown by the phantom line of FIG. 6. Thereafter, the pulling rod 311 together with the needle body 32 can be processed and discarded.

The infusion catheter 4 is a general dropper-used infusion hose. A front end of the infusion catheter 4 is connected with a connecting head 41 for connecting with the third connecting section 13 of the trifurcate connector 1.

Figure 4:
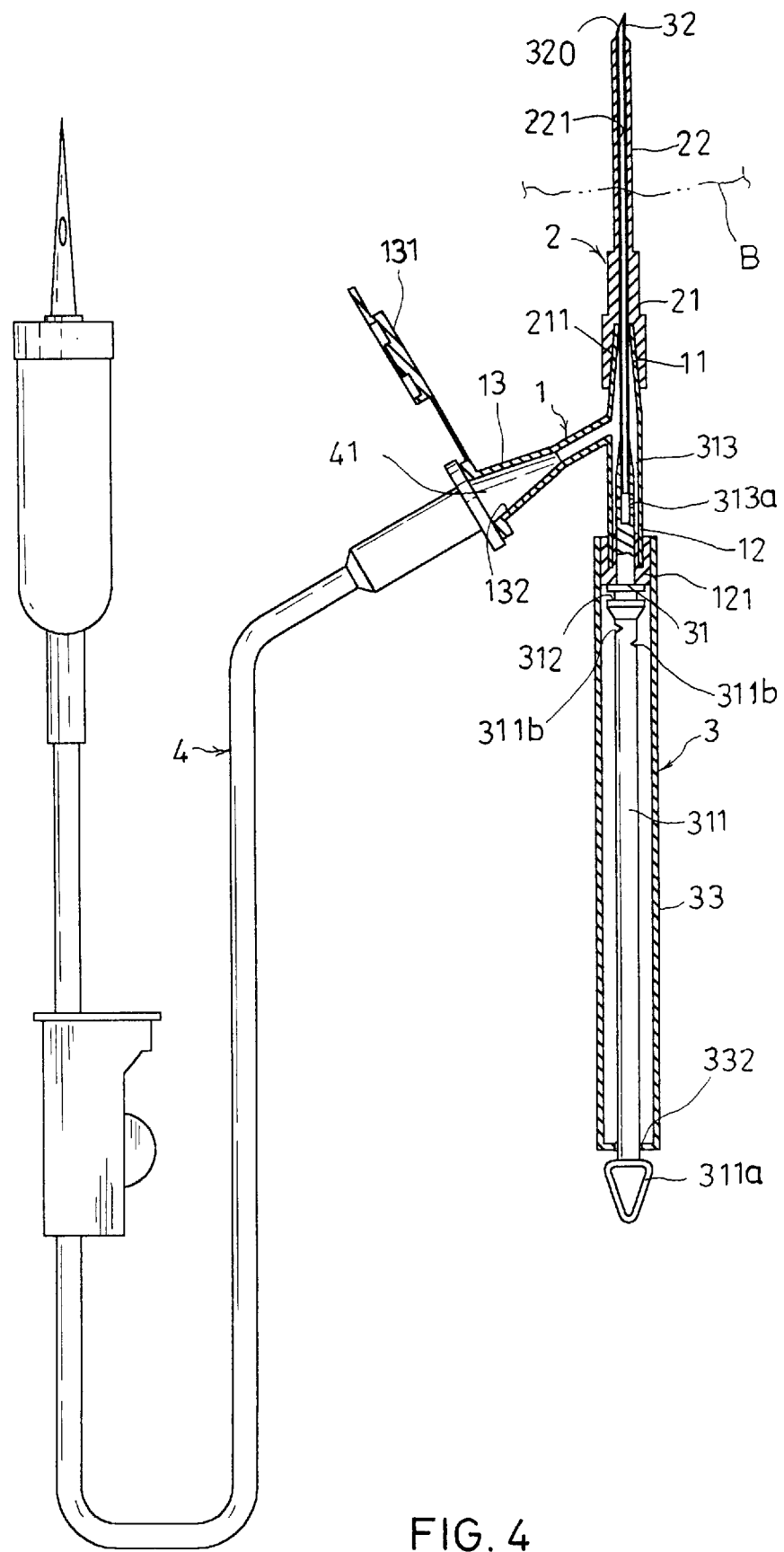
FIG. 4 is a sectional view showing that the steel needle is fitted in the soft needle for thrusting into the body of a patient.
Figure 5:
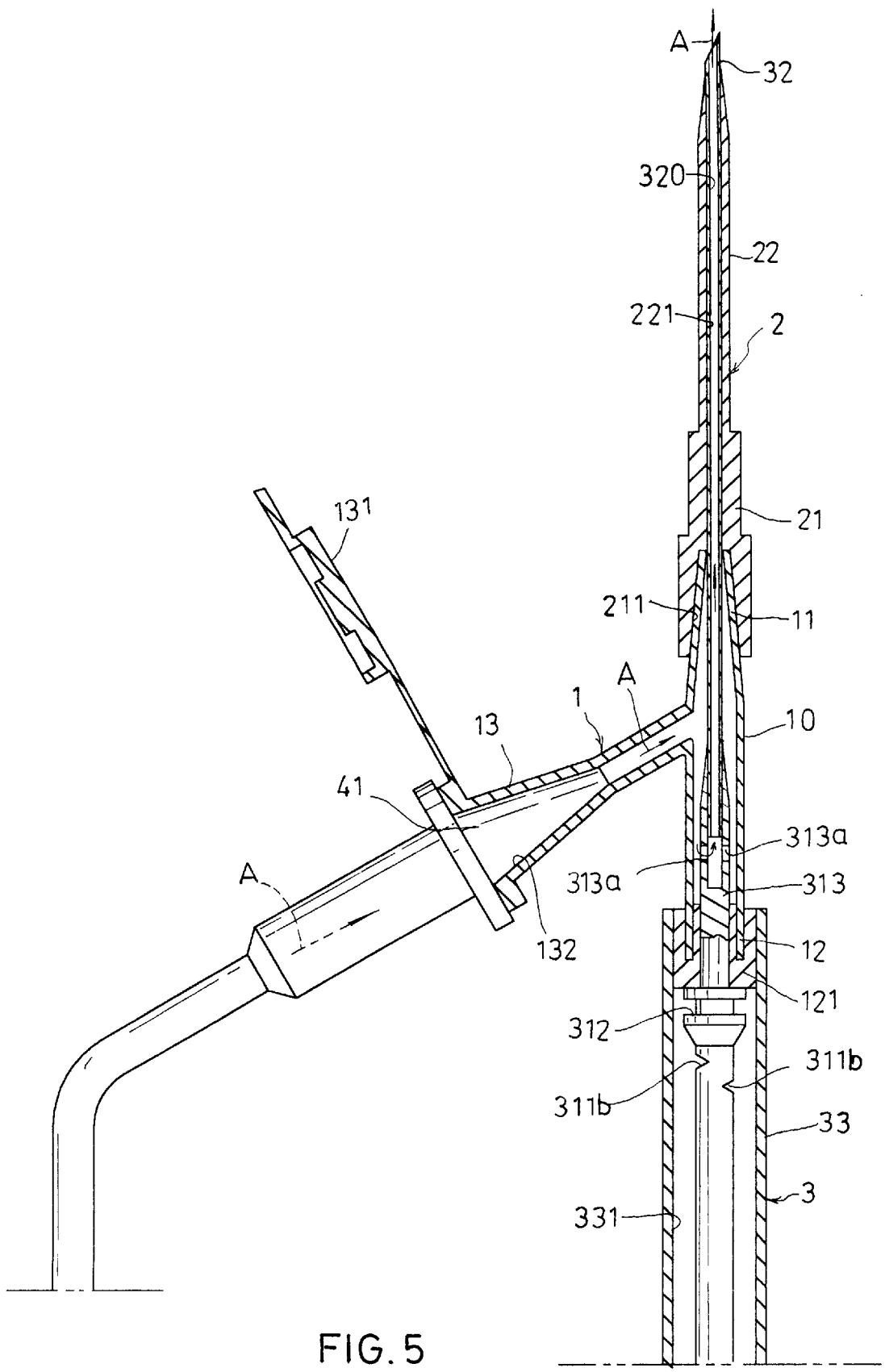
FIG. 5 is an enlarged view of a part of FIG. 4.

In use, the connecting head 41 of the infusion catheter 4 is first connected with the third connecting section 13 of the trifurcate connector 1. Then the needle sheath 23 is removed from the soft needle 2. At this time, as shown in FIGS. 4 and 5, the air contained in the infusion catheter 4 is exhausted outside through the air guiding hole 313a of the projecting post of the steel needle 3 and the central through hole 320 of the needle body 32. Therefore, the liquid medicine contained in a dropper (not shown) can smoothly flow out through the air guiding hole 313a of the projecting post 313 and the central through hole 320 of the needle body 32. This makes the infusion catheter 4 and the trifurcate connector 1 full of the liquid medicine so as to prevent the air in the infusion catheter 4 from being injected into human body to cause accident. At this time, the needle body 32 of the steel needle 3 is slidably fitted in the soft needle body 22 of the soft needle 2, providing a sufficient strength therefor to smoothly thrust into the vein of a patient B. The rubber cap 121 fitted with the end of the second connecting section 12 resiliently surrounds the projecting post 313 of the steel needle 3, so that the liquid medicine flowing from the infusion catheter 4 into the trifurcate connector 1 will not leak from the second connecting section 12. As shown in FIG. 6, thereafter, the medical personnel can pull the pulling rod 311 at the handle section 311a to draw back the holder body 31 into the sleeve 33. At this time, the needle body 32 is also drawn back out of the soft needle body 22 into the sleeve 33. When the needle body 32 is totally drawn out of the rubber cap 121, the rubber cap 121 resiliently seals the perforation thrusted by the projecting post 313 and the needle body 32. That is, the opening of the second connecting section 12 of the trifurcate connector 1 is again sealed. Further, the engaging section 312 of the holder body 31 is engaged with the latching section 332 of the sleeve 33 so as to firmly locate and hide the needle body 32 in the sleeve 33. At this time, the medical personnel can be bend and break the pulling rod 311 at the breaking notch 311b as shown by the phantom line of FIG. 6. When pulling back the needle body 32, the liquid medicine flowing from the third connecting section 13 into the trifurcate connector 1 will automatically flow from the first connecting section 11 through the soft needle 2 into the body of the patient B. Then, as shown in FIG. 7, the medical personnel can detach the sleeve 33 along with the steel needle 3 hidden therein from the second connecting section 12 for further processing and disposal. In the case that it is necessary to inject other liquid medicine, an injection syringe can be thrusted into the rubber cap 121 at the end of the second connecting section 12 to perform the injection procedure.

According to the above arrangements, the present invention has the following advantages:

1. The needle body 32 of the steel needle 3 is engaged with and hidden in the sleeve 33 without protruding outside.

Therefore, the impalement of medical personnel can be avoided and the safety in medical waste processing can be ensured.

2. When removing the needle body 32 of the steel needle 3 from the soft needle body 22, it is unnecessary to press the soft needle 2 with one hand as the conventional device. Therefore, the injection procedure can be performed more easily and leisurely.

3. The present invention has simple structure and can be easily assembled.

It is to be understood that the above description and drawings are only used for illustrating some embodiments of the present invention, not intended to limit the scope thereof. Any variation and derivation from the above description and drawings should be included in the scope of the present invention.

What is claimed is:

1. An automatic safety infusion catheter needle comprising:

a trifurcate connector having a hollow main body, an upper section of the main body being defined as a first hollow connecting section, a lower section of the main body being defined as a second hollow connecting section, the first and second connecting sections being coaxially aligned with each other about a central axis of the main body, a free end of the second connecting section being inserted with a rubber cap, a third connecting section outward projecting from the first and second connecting sections of the main body for connecting with a connecting head of an infusion catheter;

an infusion soft needle including a needle holder formed with a fitting socket at bottom end for fitting with the first connecting section of the trifurcate connector, a soft needle body connecting with and upward extending from a top end of the needle holder; and a steel needle including a holder body slidably fitted in a sleeve, a top section of the sleeve being fitted with the second connecting section of the trifurcate connector, the steel needle further including a projecting post upward axially extending from top end of the holder body, the projecting post normally penetrating beyond the rubber cap, the projecting post being formed with a radial air guiding hole, a needle body axially upward extending from upper end of the projecting post, a central through hole of the needle body being communicated with the air guiding hole of the projecting post, the needle body being slidably fitted in the soft needle body of the soft needle, the holder body being disposed with an engaging section which can be downward slided to engage with a latching section of the sleeve, whereby the needle body of the steel needle can be drawn out of the soft needle body and firmly located and hidden in the sleeve, whereby the connecting head of the infusion catheter is connected with the third connecting section of the trifurcate connector for infusion of liquid medicine through the soft needle into the body of a patient.

2. An automatic safety infusion catheter needle as claimed in claim 1, wherein the steel needle has a pulling rod axially extending from a bottom end thereof, a bottom end of the pulling rod protruding out of the bottom end of the sleeve and having a handle section.

3. An automatic safety infusion catheter needle as claimed in claim 2, wherein the pulling rod is formed with at least one breaking notch.

4. An automatic safety infusion catheter needle as claimed in claim 1, wherein the engaging section of the holder body of the steel needle is in the form of an annular groove formed on a periphery of the holder body, while the latching section of the sleeve is in the form of an inward extending flange formed on bottom edge of the fitting hole of the sleeve.

5. An automatic safety infusion catheter needle as claimed in claim 1, wherein the engaging section of the holder body of the steel needle is in the form of an annular insertion recess formed on the bottom thereof, while the latching section of the sleeve is in the form of an annular upward projecting wall formed on the bottom end thereof.

6. An automatic safety infusion catheter needle as claimed in claim 1, wherein the engaging section of the holder body of the steel needle is in the form of an L-shaped cavity formed on the periphery thereof, while the latching section of the sleeve is in the form of a projecting pin projecting from the wall of the fitting hole of the sleeve.

7. An automatic safety infusion catheter needle as claimed in claim 1, wherein an outer cap is connected with outer edge of the third connecting section of the trifurcate connector for normally sealing an opening of the third connecting section.

* * * * *